United States Patent [19]
Goodman et al.

[11] Patent Number: 4,587,046
[45] Date of Patent: May 6, 1986

[54] DRUG-CARRIER CONJUGATES

[75] Inventors: Murray Goodman, La Jolla; Neal Castagnoli, San Rafael; Kenneth Jacobson, Laguna Beach; Kenneth L. Melmon, Woodside; Roberto P. Rosenkranz, Menlo Park; Michael S. Verlander, Del Mar, all of Calif.

[73] Assignee: The Regents of the University of California, Berkeley, Calif.

[21] Appl. No.: 379,463

[22] Filed: May 18, 1982

[51] Int. Cl.$^4$ .................. C07C 103/52; C07C 101/72
[52] U.S. Cl. ................................ 530/330; 562/445; 530/331
[58] Field of Search ................ 260/112.5 R; 562/445

[56] References Cited

U.S. PATENT DOCUMENTS

| | | | |
|---|---|---|---|
| 3,704,282 | 11/1972 | Spector | 260/112.5 R |
| 3,998,799 | 12/1976 | Bodor et al. | 424/177 |
| 4,116,949 | 7/1978 | Goodman et al. | |
| 4,318,847 | 3/1982 | Umezawa et al. | 260/112.5 R |
| 4,337,207 | 6/1982 | Goodman et al. | 260/112.5 R |
| 4,426,324 | 1/1984 | Meienhofer | 260/112.5 R |

FOREIGN PATENT DOCUMENTS 1058828 2/1967 United Kingdom .

OTHER PUBLICATIONS

Ringsdorf, Journ. of Polymer Science Symposium 51, 135–153 (1975).
Donaruma, Progress in Polymer Sciences 4, 1–25 (1975).
Batz, Advances in Polymer Science 4, 25–53 (1977).
Godeau et al., Proc. Nat. Acad. of Sciences USA 75, 2353–2357 (1978).
Ringsdorf et al., Die Makromoleculare Chemie 177, 741–746 (1976).
Melmon et al., Journ. of Clinical Investigation 53, 22–30 (1974).
Shear et al, Journ. of Bio. Chemistry 251, 7572–7576 (1976).
Poon et al., Molecular Pharmacology (1977).
Pitha et al., Proc. of Nat. Acad. of Science USA 77, 2219–2223 (1980).
Verlander et al., Proc. Nat. Acad. of Sciences USA 73, 1009–1012 (1976).
Venter et al., Polymeric Delivery Systems, Midland Macromolecular Symposium No. 5, 237–250 (1978).
Goodman et al., Journ. of Macromolecular Science Chemistry, A13, 529–543 (1979).
Hu et al., Molecular Pharmacology 14, 237–245 (1977).
Melmon et al., Molecular Pharmacology 12, 701–710 (1976).
Weinstein et al., Journ. of Clinical Investigation 52, 1349–1361 (1973).
Reitz et al, Journ. of Organic Chemistry, (1982).
Verlander et al., IUPAC International Symposium on Macromolecules, Sep. 1980.

*Primary Examiner*—Delbert R. Phillips
*Assistant Examiner*—F. T. Moezie
*Attorney, Agent, or Firm*—Phillips, Moore, Lempio & Finley

[57] ABSTRACT

Biologically active drugs, e.g. catecholamine hormones, are coupled to carrier molecules, e.g. monodisperse peptides to produce conjugate molecules. The conjugate molecules retain biological activity, but the pharmacokinetic, pharmacodynamic and/or potency properties of the drug is modified. The drug is coupled to the carrier via a spacer moiety which not only serves to covalently link the drug to the carrier, but also insulates the biologically active portion of the drug, i.e., the pharmacophore, from degradation during the coupling process. The carrier preferably consists of a monodisperse peptide in which the sequence of amino acid residues is carefully preselected and controlled.

16 Claims, No Drawings

DRUG-CARRIER CONJUGATES

DESCRIPTION

1. Field of The Invention

This invention relates to the coupling of biologically active molecules or derivatives of such molecules with organic carriers to thereby modify the pharmacokinetic, pharmacodynamic and/or potency properties of the naturally occurring bio-active molecules i.e., drugs. The coupling preferably requires the presence of a suitable spacer moiety which links the naturally occurring drug, or a derivative, to the carrier. Thus the drug derivative is covalently bound to the carrier. The carrier may be any of a broad range of organic moieties which may either be themselves biologically active, but more usually are biologically acceptable in vivo. Peptides are especially suitable as carriers.

2. Background of the Invention

In the past there has been extensive work by a number of pharmaceutical and chemical investigators on techniques for chemically altering and/or modifying the bio-activities of naturally occurring bio-active molecules. These investigations have attempted to alter or modify such molecules in an effort to increase specific bio-activity, prolong bio-activity, reduce toxic effects, reduce or eliminate side effects, narrow the biological activity, or change biologic specificity. Very often chemical modification of bio-active molecules removed or greatly reduced bio-activity, but in some instances bio-activity has been enhanced, modified or changed in a useful way. In view of past successes there has been extensive investigation into the chemical modification of bio-active molecules in an effort to usefully influence their activity.

Numerous studies have been made on the covalent bonding of bio-active molecules (drugs) to some type of physiologically acceptable carrier for the purpose of modifying bio-activity. Thus it is expected that the carrier may either affect the intensity of activity, shorten or prolong the activity, redirect the activity, and/or reduce side effects, etc. of the drug. On the other hand, a carrier coupled as an integral part of the bio-active molecule introduces a large number of additional variables which may affect the activity and acceptability of the modified drug in an in vivo environment. The carrier could block the biological activity, i.e., interfere with the pharmacophore's ability to bind to its normal receptors; or it may itself exhibit bio-activity antagonistic to that of the pharmacophore; or the carrier may prove to be antigenic and invoke a response from the host immune system, etc. Therefore the selection and preparation of a useful and acceptable drug-carrier system potentially presents a number of problems. Nonetheless, the potential advantages to be gained utilizing such drug modification techniques has led to continued investigations in this area.

As used herein the term "drug" shall mean any molecular entity, e.g. a hormone, which has specific biological activity. "Pharmacophore" shall mean the bio-active or binding site portion of a drug molecule. The term "congener" shall mean a drug that has had its molecular structure chemically modified to form a functionalized derivative. The term "carrier" shall mean a physiologically acceptable molecular structure, e.g. a peptide, that is used to covalently bind to a drug in its congener form. The term "spacer" means a bridging chemical grouping that modifies the drug structure to remove the pharmacophore from close proximity of the carrier. The spacer has a functional group added at the end thereof to facilitate attachment of the drug to the carrier. The drug plus attached spacer and associated functional group comprise a "congener". The drug is linked through the spacer and the associated functional group to the carrier to form a "conjugate". Other terms will be defined where necessary as they occur in the following description.

A number of prior investigators have shown that it is possible to alter pharmacological properties of certain biologically active molecules through covalent attachment to carriers without losing their ability to bind at a receptor and to stimulate biological activity. Donaruma et al. in the monograph "Polymeric Drugs" Academic Press, New York 1978 and Gregoriadis in "Drug Carriers in Biology and Medicine" Academic Press London, 1979, as well as the articles by Ringsdorf in the Journal of Polymer Science Symposium No. 51, 135-153 (1975); and Donaruma in Progress in Polymer Science 4, 1-25 (1975); and Batz in Advances in Polymer Science 23, 25-53 (1977) review a number of examples of drugs which have been bound covalently to soluble or insoluble polymers which may be either natural or synthetic. For example, Weiner and Zilkha noted in the Journal of Medicinal Chemistry 16, 573-574 (1973) the attachment of a local anesthetic, procaine, to polyethylene oxide. They found that the conjugate remained biologically active and had a prolonged duration of action. Godeau et al. in The Proceedings of the National Academy of Sciences, USA, 75, 2353-2357 (1978) reported linking a progesterone analog to polyethylene oxide. The conjugate retained activity to induce maturation in certain oocytes sites. Ringsdorf et al. in Die Makromoleculare Chemie, 177, 741-746 (1976) observed anti-viral activity in polymethacrylate derivatives of 1-adamantaneamine.

The group of sympathomimetic hormones which are known as catecholamines because of their chemical structures form a class of bio-active compounds which are suitable drugs for attachment to carrier moieties. The receptors for catecholamines are located on the outer surface of cell membranes and the observed biological effect of the attachment of such hormones to carriers need not be dependent upon, or complicated by, complex membrane transport phenomena or phagocytosis of a conjugate molecule. It is possible for covalent conjugates of the catecholamines to reach the catecholamine receptor sites intact.

On the other hand, the catecholamines themselves have several clinical limitations such as, rapid systemic depletion, problems arising from lack of tissue specificity, and decrease in responsiveness to the drug, which also enhance their candidacy for attachment to carrier moieties. It is to be expected that carrier-attached catecholamines might be degraded less readily by enzymes; and that the carrier might also impart greater specificity to the drug action.

Other drugs which have related structures and suffer from similar limitations to those outlined above are also suitable candidates for covalent attachment to carriers. These drugs include other sympathomimetic drugs such as dopamine, phenylephrine, the amphetamines, ephedrine and related drugs; and also the so-called autacoids, which include histamine, 5-hydroxytryptamine (serotonin), the prostaglandins and related compounds. For the purpose of the discussion that follows, it should be understood that where reference is made to "the drug" or "the catecholamine", these other related drugs are meant to be included.

The chemical structure of the principal cathecholamine hormones are as follows:

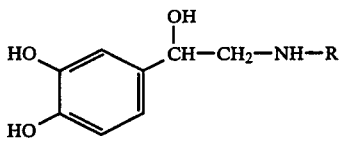

where R may be —H (norepinephrine); —CH₃ (epinephrine); —CH(CH₃)₂ (isoproterenol).

There are a number of compounds closely related to the catecholamines which also exhibit physiological effects, principally as $\beta_2$ agonists (glands, smooth muscle, lungs). Such related compounds include the resorcinolamines:

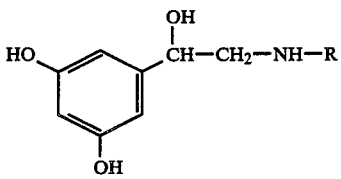

where R may be —CH(CH₃)₂ (metaproterenol);

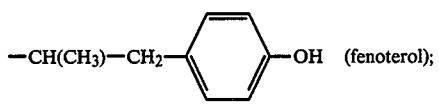  (fenoterol);

—C(CH₃)₃ (terbutaline); and the saligenin derivative:

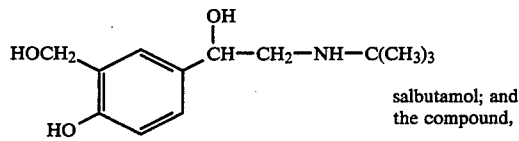

salbutamol; and the compound,

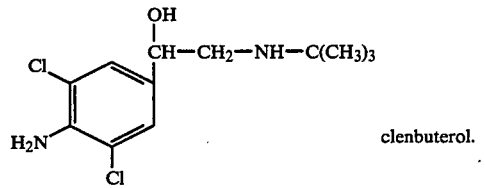

clenbuterol.

For convenience, when catecholamines are hereafter mentioned, all such related compounds are also meant to be included.

Other sympathomimetic drugs include:

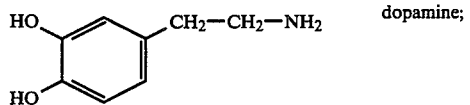 dopamine;

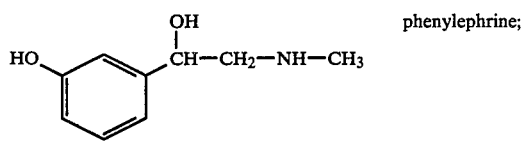 phenylephrine;

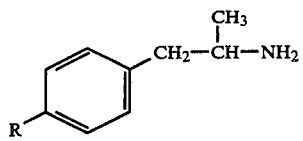

the amphetamines, where R may be H (amphetamine) or OH (hydroxyamphetamine);

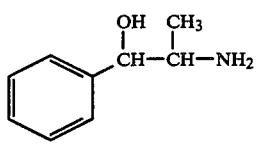 phenylpropanolamine; and

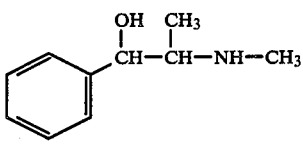 ephedrine.

The structures of the important autacoids are:

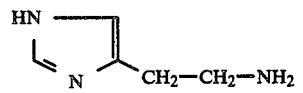 histamine;

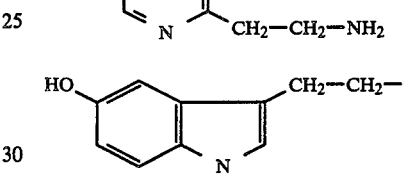 5-hydroxytryptamine (serotonin); and

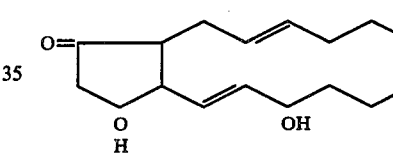 prostaglandin E₂.

Norepinephrine is a primary phenethylamine, while epinephrine is its N-methyl derivative. Isoproterenol is the synthetic N-isopropyl analog of epinephrine with selective β-adrenergic activity. In all instances the phenyl ring contains hydroxyl groups in an ortho orientation (catechol). The basic catecholamine hormones are associated with the contraction of smooth muscle tissue (alpha-adrenergic response); and the relaxation of smooth muscle tissue (beta-adrenergic response). The catecholamines also stimulate the sympathetic nervous system and are clinically useful drugs for the modulation of endocrine-cardiovascular and renal functions. Some of the catecholamine hormones e.g. isoproterenol act as bronchodilators, as heart stimulants, etc.

Other related sympathomimetic drugs have a variety of effects which include actions on peripheral and cardiovascular α- and β-adrenergic receptors, metabolic effects and effects on the central nervous system. The autacoids also have a similarly broad range of effects. Histamine, for example, both stimulates the contraction of smooth muscle, such as those of the bronchi and gut and also relaxes others, such as those of fine blood vessels, as well as stimulating the production of gastric acid and eliciting various other exocrine secretions. 5-Hydroxytryptamine (serotonin) is responsible for a wide variety of effects in the cardiovascular, respiratory and gastrointestinal systems. The prostaglandins have even more diverse actions which include vasodilation, inhibition of platelet aggregation, contraction or relaxation of smooth muscle, central nervous system, endocrine and metabolic effects.

Catecholamines are deactivated metabolically by several routes and, as a result, have short durations of action in vivo. Catechol 0-methyl transferase methylates the hydroxyl group at the three position and the product is inactive. Sulfonation of the same hydroxyl group also occurs in vivo, mainly in the intestines, accounting for inactivation after oral administration. Catecholamines are also labile to enzymatic and nonenzymatic oxidation producing adrenochromes and other inactive species.

Like the catecholamines, other sympathomimetic drugs and autacoids also undergo similarly complex metabolic deactivation processes in vivo which severely limit their clinical usefulness as drugs.

Because of the above-noted in vivo limitations, catecholamine hormones and the other related drugs noted above are prime candidates for modification through covalent bonding to carrier moieties.

Catecholamine hormones have been immobilized on porous glass beads (see Kaplan et al., Proceedings of the National Academy of Sciences USA 69, 1141-1145 (1972); Proceedings of the National Academy of Sciences USA 70, 1214-1217 (1973); Proceedings of the National Academy of Sciences USA 72, 824-828 (1975); Methods in Enzymology 38, 180-186 Academic Press (1974)). The hormones were bound via diazotization onto arylamine glass. The glass bound drugs demonstrated dramatic ability to increase heart rate in anesthetized dogs and in chick embryos and to stimulate cyclic AMP production in cultured glial tumor cells. These immobilized catecholamines also had a positive inotropic effect on isometrically-contracting cat papillary muscles. Linkage to the glass beads occurred via an arylazo group attached to the hormone ring structure. Although the observed bio-activity was attributed to the covalently bound hormone-glass species there have been observations that, in fact, there was some decoupling of hormone from the porous glass. The decoupled hormone would therefore be available to produce the observed biological effects.

Several investigators (see Melmon et al., Journal of Clinical Investigation 53, 22-30 (1974); Shear et al. Journal of Biological Chemistry 251, 7572-7576 (1976); Poon et al., Molecular Pharmacology, 1977) immobilized catecholamines and other autacoids onto Sepharose through amino groups and via a random copolypeptide system and proteins as affinity attractants for lymphocytes having receptors. Cells which were responsive to the hormones were bound to the support and could be displaced by competitive antagonists or by high concentrations of hormones.

Pitha et al. in Proceedings of the National Academy of Sciences USA 77, 2219-2223 (1980); Verlander et al. in Proceedings in the National Academy of Sciences USA 73, 1009-1012 (1976); Venter et al. in Polymeric Delivery Systems, Midland Macromolecular Symposium No. 5, 237-250 (1978); Goodman et al. in Journal of Macromolecular Science - Chemistry, A13, 529-543 (1979); Hu et al. in Molecular Pharmacology 14, 237-245 (1977); Melmon et al. in Molecular Pharmacology 12, 701-710 (1976); and Weinstein et al. in Journal of Clinical Investigation 52, 1349-1361 (1973) reported soluble conjugates of beta agonists and antagonists and autacoids. In the work of Verlander, Goodman and their co-workers isoproterenol was bound to a random copolypeptide by the same chemical means utilized in the porous glass binding. Random copolymers containing hydroxypropylglutamine and p-aminophenylalanine were diazotized and coupled with isoproterenol. The hormone was bonded to the peptide via an azo group. The azo group was coupled to the hormone at the six carbon position on the catechol ring structure. Such coupled hormone-azopeptide structures exhibited substantial biological activity and prolonged biological effect.

Melmon et al. in Molecular Pharmacology 12, 701-710 (1976) and in the Journal of Clinical Investigation 52, 1349-1361 (1973) reported catecholamine conjugates wherein catecholamines and autacoids were coupled to albumin or to a random copolymer of alanine and tyrosine. Norepinephrine was coupled to primary amines of the carriers by condensation with a bifunctional reagent, glutaraldehyde. The resulting diimine was reduced with sodium borohydride to the di-substituted diamine. Coupling by such means, however, does not yield a single product. Two drugs of the same type may be linked to one another, or two carriers may be joined together. Thus the desired conjugate yields in such coupling reactions can be very low. It is not possible to predict the structure of the resulting conjugates.

All such prior reported catecholamine conjugates suffered from low yields of products whereby the techniques are of no economic importance or the reaction products yield a "gemisch" of products which may or may not be conjugates; and if conjugates the chemical structure thereof is unpredictable and/or very difficult to determine. Thus it is desirable to develop techniques for producing conjugates in good yield; with predictable and specific chemical structures; and yet retain and/or exhibit at least one or more of the desired biological activities of the drug component.

BRIEF DESCRIPTION OF THE INVENTION

The present invention deals with drug-carrier conjugates, specifically conjugates of the bioactive catecholamine hormones, related sympathomimetic drugs and autacoids that have been attached to carrier moieties that have been chemically precisely defined. The use of such precisely defined carriers and the particular methods for producing the conjugates therefrom results in conjugates whose chemistry is fully defined, thus facilitating the interpretation of their biological activity. The conjugates of the present invention, which are derived from precisely defined carriers, permit more efficient methods for purification and detection of impurities.

More specifically, the present invention contemplates the preparation of conjugates linking a functionalized drug (congener), e.g., a catecholamine hormone derivative, to a carrier molecule, e.g., a peptide, by covalent bonds. A functional spacer is utilized for covalent linkage to the drug and to the carrier, yet it does not interfere with the pharmacological properties of the drug. It also provides a chemically stable linkage with the carrier; and facilitates good yields of the conjugate.

The conjugates of the invention may be most easily conceptualized from the following:

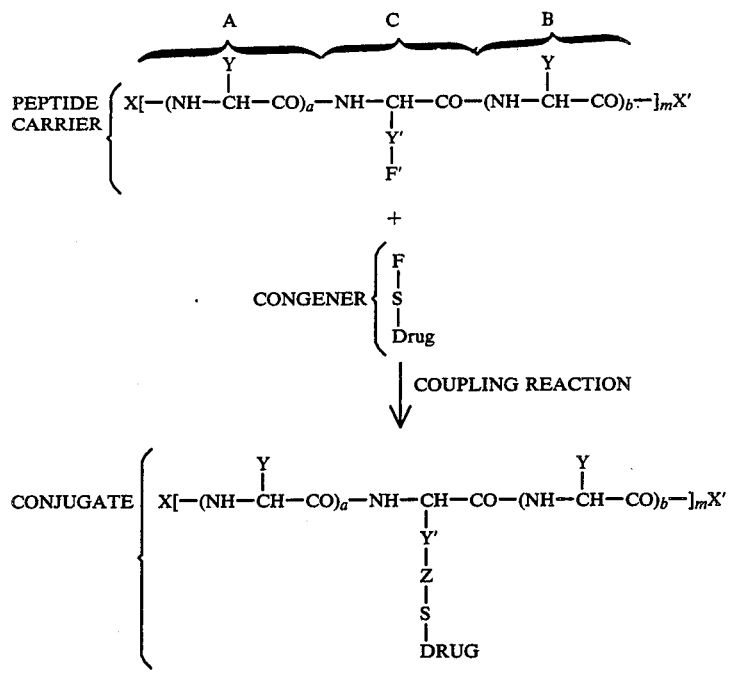

where:

S is a schematic representation of the spacer group attached to the drug; and

F is a schematic representation of the functional group attached to the spacer, where Drug-S-F comprise the congener;

F' is a schematic representation of a functional group attached to the carrier side chain, Y', of the amino acid residue to which the congener is bound and wherein the functional group F' is reactive with functional group F;

Z is a schematic representation of the reacted groups F and F' whereby the congener is bound to the carrier.

A,B are oligopeptide blocks wherein the amino acid residues are the same, or different with predesigned sequences.

C is an amino acid residue to which the congener is bound.

X is an amine blocking group, or —H

X' is a carboxyl blocking group, or —H

Y is a general amino acid residue side chain

Y' is a side chain on the amino acid residue to which the congener is bound a=b; a≠b; a or b can be 0, or any small integer and m=1,2,3, etc.

As will be apparent from the general structure above, the drug is bound via a spacer and reacted functional group moiety, Z, to the C amino acid residue side chain Y' of the carrier peptide A-C-B. The carrier consists of a monodisperse peptide wherein blocks A and B may be homo-oligopeptide blocks, i.e., wherein the amino acid residues are identical, or alternately, several different amino acid residues in a predetermined sequence. A particular amino acid residue, C, is positioned at a predetermined position in the peptide chain. Amino acid residue, C, which consists of a single amino acid residue, is selected to be reactive with the particular congener to be attached to the carrier.

It should also be understood that the peptide carrier blocks A,B and C may be linked with homologous blocks A,B and C to form carrier peptides of increasingly greater molecular weights, e.g., $[A\text{-}C\text{-}B]_m[A\text{-}C\text{-}B]_n$, where m=1,2,3, etc. and n=0,1,2,3, etc. and where the sequence of blocks A,B, and C in the peptide chain may be of any desired order. It should also be understood that peptide blocks A-C-B may be linked to a defined peptide sequence D, such as a naturally-occurring peptide or protein. Thus any desired molecular weight or sequence of monodisperse peptides may be utilized as the carrier moiety of the conjugate.

It should also be understood that the carrier may consist of but a single blocked amino acid residue, C, alone. Selection of the number of amino acid residues and their identity will be discussed hereinafter. Generally speaking, however, carrier moieties having molecular weights in the range of $2 \times 10^2$ to $10^4$ daltons seem to be most suited for maintaining the rapid onset of biological activity in vivo. Nonetheless carrier molecular weights of $10^5$ daltons or greater are also contemplated for use in the conjugates of this invention.

Naturally-occurring monodisperse peptides are also contemplated for use as carriers for drugs in the manner already described for synthetic, monodisperse carriers. Thus, peptide hormones and proteins are useful in this context since they naturally contain functional groups (e.g. amine or carboxyl groups) provided by the side chains of their constituent amino acids. Antibodies, especially monoclonal antibodies, are particularly useful as carriers for drugs since, because of their specificity for particular cells, they can be used to target the drugs and thereby optimize the activity of the drug while minimizing or eliminating side effects.

The spacer moiety may include an alkyl, aryl, arylalkyl, alkenyl, polyenyl group, so long as said group does not interfere with the coupling of the congener to the carrier. It is advantageous that the spacer group incorporate a branched chain immediately adjacent to the amine group of the drug in the case of the catecholamines, since this is known to be important for enhancing β-adrenergic activity. The spacer moiety must be capable of covalently bonding to the terminal end of the amine side chain of the drug; while also being capable of covalently bonding to the reactive group of the carrier molecule.

Certain drugs such as the prostaglandins can be considered to already possess a spacer group and a functional group in their naturally-occurring form, and therefore an additional spacer group may not be required for attachment to carriers.

The spacer moiety attached to the drug may be any group as noted above. The initial end of the spacer moiety must be capable of covalently bonding to the terminal end of the amine side chain of the drug; while its terminal end must be bonded to a functional group, which group must, in turn, be capable of covalent bonding to side chain Y', of the carrier amino acid residue, C. The functional group terminal end is chosen to be complementary to the functional group terminating side chain, Y' of the carrier amino acid residue, C. Thus if residue C side chain contains an amine functional grouping, e.g. lysine or p-aminophenylalanine, the terminal functional grouping of the attached functional group may be a carboxyl, a sulfonic acid, etc.

The number of drug congeners per conjugate molecule may be one, or any number greater than one. Wherever an amino acid residue, C, is placed within the carrier structure a drug congener may attached thereto. The greater the number of the C amino acid residues present in the carrier the greater the number of drug congeners that may be attached. The spacing between the drug congeners on any conjugate molecule may also be controlled by the spacing of the C amino acid residues on the carrier blocks. Thus the size and sequence of the oligopeptide blocks A and B (note the variables a and b in the general structure diagram above) will determine the spacings between the C peptide residues and thus the spacings between the attached drug congeners. Similarly, the sequence in which the oligopeptide blocks A,B and C are present in the carrier molecule will also determine the distances between attached drug congeners.

Similarly, when naturally-occurring, monodisperse peptides are used as carriers, although the sites of attachment may remain constant, because of the defined sequence of the peptide or protein, the number of drug molecules per carrier molecule may be controlled through the stoichiometry used during the coupling reaction.

The amino acid residues in the synthetic peptide carrier molecule may be present either in the L-form or in the D-form, or as a mixture of both forms. Incorporation of D-amino acid residues into the carrier increases proteolytic resistance of the conjugates in vivo. Increased proteolytic resistance should also affect the duration of the effect of the attached drug.

Generally, the conjugates of the invention are synthesized by one of two routes. The first method involves the preparation of appropriate congeners wherein the extended amino side chain of the drug has a suitable spacer moiety terminated in a functional group added to the amino end of the drug. The functionalized drug i.e., the congener, is then, in turn, coupled to the side chain Y' of the C amino acid residue in the carrier peptide. The second method of synthesis involves the initial modification of the carrier peptide by coupling the spacer-functional group moiety directly to the side chain, Y', of the C amino acid residue. The resulting peptide-functional group-spacer is then coupled directly to the catecholamine, for example, by a reductive amination reaction to produce the peptide-drug conjugate.

It is therefore an object of the invention to provide biologically active drug conjugates.

It is another object of the invention to provide drug conjugates that have precisely defined structures.

It is yet another object of the invention to provide catecholamine-peptide conjugates.

It is still another object of the invention to provide chemically efficient methods for producing drug conjugates.

It is still another object of the invention to provide functionalized catecholamine congeners which may be covalently bound to monodisperse peptide carriers.

Other objects and advantages of the invention will be apparent from the description herein as well as the claims pending hereto.

DETAILED DISCLOSURE OF THE INVENTION

The conjugates of the invention comprise catecholamines linked to monodisperse peptide carriers through an intermediate spacer-functional group moiety. The catecholamine drug may be derived from any one of a number of bio-active catecholamines, or related adrenergic compounds such as those compounds noted above which contain suitable pharmacophores for use in the conjugate structures. It is of considerable importance that the bio-active site (pharmacophore) be stable under the conditions imposed during conjugate synthesis; and that the bio-active site be remote from the point of attachment to the spacer moiety and carrier. Previous studies have indicated that, in the case of the catecholamines, the bio-active site is closely associated with the catechol end of the molecule. Therefore, it is important that drugs be attached to the carrier at as remote a position as possible from this grouping, i.e., at the alkyl amine end of the catecholamine side chain.

It has been determined that the biological activity of the pharmacophore portion of the drug may be preserved if a spacer moiety is interposed between the drug and the carrier to which the drug is attached. Such a spacer comprises a chain structure, e.g. an alkyl grouping or branched alkyl group having from two up to five or more carbon atoms in the chain, i.e., a chain of methylene groups

(R=H or CH$_3$ or higher alkyl). The spacer grouping also must be terminated by a functional group which is capable of covalently linking with the side chain, Y' of the preselected amino acid on the carrier peptide. The terminating functional group may be, for instance, a carboxylic acid or a sulfonic acid, etc.

The drug and attached spacer comprise the congener molecule which is linked to the carrier peptide.

The congeners may be prepared from the drug by reductive amination, for example with a methyl ketoacid. For example, if the drug is norepinephrine:

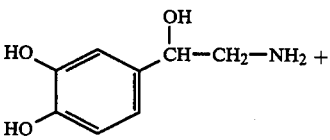

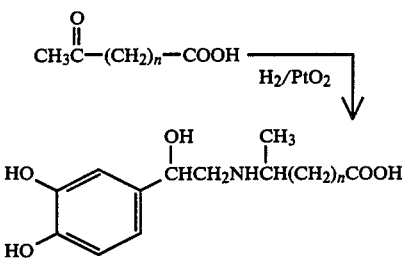

Similarly, the other drugs described above may be derivatized in an analogous manner.

Some typical carboxyl-containing congeners prepared from norepinephrine by the above methods are set forth in Table 1 below:

TABLE 1

Synthesis of Carboxylic Acid Congeners of Isoproterenol

| Compound | n = | % yield[b] | M.W. |
|---|---|---|---|
| A | 2 | 51 | 269.30 |
| B | 2[a] | 79 | 269.30 |
| C | 3 | 50 | 283.33 |
| D | 4 | 65 | 297.36 |
| E | 5 | c | 311.38 |

[a]prepared from D—norephinephrine; $[\alpha]_D^{25}$ of product = 23.7°.
[b]prior to purification by HPLC.
[c]nearly quantitative.

A detailed description of the preparation of some catecholamine congeners and model amides is set forth in U.S. patent application Ser. No. 184,000 filed Sept. 4, 1980 and entitled "Biologically Active Catecholamine Derivatives," which description is incorporated hereinto by reference.

The Carrier

For the purposes of the present invention, monodisperse peptides which may be synthetic or naturally occurring are most useful as the carrier portion of the drug conjugate. It is important that the amino acid sequences in the peptide carrier be completely defined and carefully controlled. As noted above for purposes of illustration, the peptide carrier may be broken down into a series of monodisperse blocks A,C,B wherein each block is linked to the others in any desired sequence. Block C consists of a single amino acid residue which is utilized as the site to which the drug congener is covalently bonded. Peptide blocks A, B are linked to block C by customary peptide linkages. However, it should be noted that blocks A,B, and C may be linked together in any desired sequence e.g., A-B-C, A-C-B, B-C-A, C-A-B, etc. The sequence of naturally-occurring peptides and proteins is, of course, completely predetermined.

The drug linkage to the carrier occurs at the side chain on the amino acid unit (block C) which is incorporated into the carrier sequence for that purpose. The spacer group previously referred to links the drug and the carrier. The type of linkage to the peptide is selected on the basis of stability and potential effect on biological activity.

In the case of naturally-occurring peptides and proteins, linkage of the drug to the carrier must take advantage of functional groups provided by the side chains of the amino acids of the natural sequence. For example, carboxyl-containing congeners (Table 1) may be attached to the side chains of lysine or ornithine or to the amine terminal amine of the peptide chain.

The other amino acids in the carrier are chosen to impart a particular set of physical and chemical properties to the resultant conjugate and thereby modify the drug's pharmacological properties. Each carrier molecule may have one or more congeners attached thereto. The number of drug molecules per carrier molecule may also affect the biological activity of the conjugate.

Peptide blocks A and B may be monodisperse homo-oligopeptide blocks or may be composed of several different amino acids depending upon the required overall properties of the carrier. For example, hydrophilic character can be imparted through the incorporation of glutamine, citrulline or hydroxyl-containing amino acids, e.g. δ-hydroxy-α-aminovaleric acid. On the other hand, hydrophobic properties are imparted through the insertion of amino acids such as alanine, valine, leucine, phenylalanine, etc. Glutamic and aspartic acids, lysine, ornithine etc. may be used to provide negatively or positively charged or zwitterionic carriers. The choice of the amino acid used at the drug binding site (block C) depends on the drug congener attached to the carrier.

In order to carefully control and fully define the amino acid sequence in the synthetic carrier peptides, the carrier molecule is built up by assembling amino acids in the desired sequence. Such peptide synthesis techniques are well known and extensively practiced. Specific examples of carrier synthesis are set forth in a number of the examples below.

During peptide synthesis a wide variety of amine and carboxyl blocking groups, X, X' may be employed. X may be a carbonyl or oxycarbonyl containing group bonded to the N-terminal amino acid residue through an amide or urethane respectively. X' may be bonded to the C terminal residue through an amide, for instance, 3-hydroxypropylamide or N-methylamide, or through an ester linkage, for instance, a methyl, ethyl or higher alkyl ester.

The carrier may range in size from a single, blocked amino acid residue to much larger peptide derivatives. The peptide blocks A-B-C may be used as the carrier or they may be linked in a specific manner to similar blocks. These well-defined specific amino acid peptide sequences are monodisperse sequence-controlled carrier molecules.

Such monodisperse peptide carrriers are of primary importance to the conjugates of the invention. Through the use of monodisperse peptide carriers, the number and spacing between the drug molecules attached to the carrier can be carefully controlled. Chromatographic characterization and the chemical analysis of the conjugate molecule are also aided by monodispersity. Monodispersity of the carrier molecule also aids in an analysis of the effect a change in various structures and parameters of the conjugate has upon drug activity.

The Conjugates

The structure and preparation of the conjugates may be understood by reference to a specific series of monodisperse conjugates wherein norepinephrine (the drug) is linked to monodisperse peptides (the carrier) to provide isoproterenol analogs. The synthesis of the conjugates is accomplished by any of several routes wherein (1) the drug molecule is first modified to produce a congener thereof. The modification of the drug to form the congener comprises linking the desired spacer grouping to the drug. The spacer grouping is terminated by a functional grouping which is then linked to a suitable amino acid residue on the carrier molecule; or (2) the carrier molecule has the spacer grouping linked to a predetermined amino acid residue in the carrier peptide chain and the drug molecule is then reacted with the functionalized carrier to form the desired conjugate. The second route is generally preferred in the case of small synthetic carriers because of increased yields and a decreased chance of degrading the pharmacophore portion of the drug during conjugate formation.

However, in the case of naturally-occurring peptide carriers, such as peptide hormones and proteins, the first route may be preferred because of the potential sensitivity of the carrier to degradation or decomposition (including denaturation) during the linking reaction of the drug to the prefunctionalized carrier in route (2).

The second method involves first attaching a keto-acid to the carrier peptide. The functionalized peptide carrier is then linked to the drug by reductive amination.

The synthesis may be illustrated schematically for the catecholamine series as:

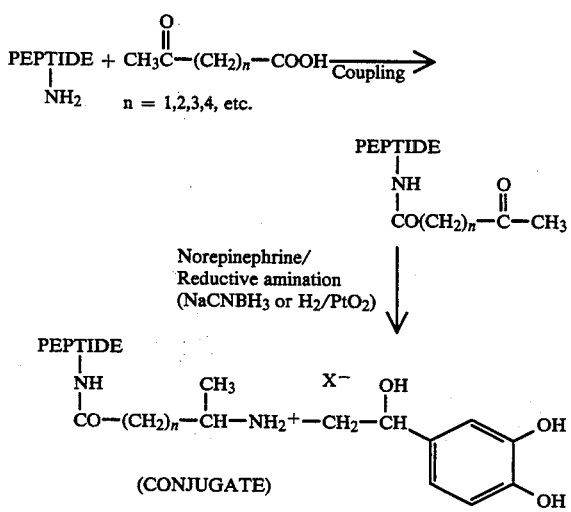

In a variation of this method, the keto-acid may first be bound to an N-protected amino acid, i.e., the amino acid of block C previously referred to above. The functionalized amino acid is then incorporated into the peptide blocks A and B, which are then reacted with the catecholamine as shown above.

More specifically and for purposes of illustration, a simple conjugate i.e., norepinephrine linked to a single amino acid (block C) e.g., p-aminophenylalanine may be considered. In this illustration the alpha amine and carboxylic acid ends of p-aminophenylalanine are blocked by the acetyl and 3-hydroxypropylamide groups respectively. The 3-hydroxypropylamide group enhances water solubility of the resultant conjugate.

In the actual procedure the amino acid p-nitrophenylalanine is first converted to the N-acetyl methyl ester derivative in two steps. One of two alternate methods may be used. In the first of these, esterification is carried out by the method disclosed by Guttman and Boissonnas in Helv. Chim. Acta. 41, 1852–1867 (1958) followed by pyridine-catalyzed acetylation. In the second method, the amino acid is first acetylated with acetic anhydride in cold, aqueous base without racemization by the procedure as set forth by Yoshida and Ishii in J. Biol. Chem. 71, 185–191 (1972). The N-acetyl-p-nitrophenylalanine is then esterified by diazomethane.

The N-acetyl methyl ester derivative, either in the L- or D-form rs then converted to the 3-hydroxypropylamide by aminolysis with an excess of 3-amino-1-propanol.

The methyl ketone functional grouping is attached to the acetyl amino acid hydroxypropylamide derivative by catalytic reduction of the nitro group followed by coupling to a keto-acid such as 6-oxo-n-heptanoic acid. The methyl ketone functionalized amino acid carrier molecule is then subjected to catalytic reductive amination with norepinephrine in the presence of acetic acid to yield the norepinephrine-amino acid conjugate. The resultant conjugate is purified by utilizing thin layer chromatography on silica gel in a polar solvent system.

Similar techniques to those outlined above, may be utilized to prepare conjugates of the catecholamines with carrier molecules having multiple amino acid residues forming the peptide. Several of such preparations are set forth in the examples hereinbelow.

Preparation of Peptide Carriers

The following examples illustrate the various methods which may be used for producing monodisperse peptide carriers.

p-Nitro-L-Phenylalanine (1)

Using the procedure of Bergel and Stock as set forth in J. Chem. Soc., 2409–2417 (1954) L-phenylalanine (50 g) was treated with a mixture of concentrated sulfuric acid (150 ml), and fuming nitric acid (28 ml) to produce the nitro compound Yield 26.9 g (43%) mp 232°–234° C., $[\alpha]_D^{25} = +9.6°$ (c=1.77, 1N HCl).

p-Nitro-L-Phenylalanine Methyl Ester Hydrochloride (2)

In an adaptation of the method of Guttman and Boissonnas [Helv. Chim. Acta, 41, 1852–1867 (1958)], thionyl chloride (distilled, 0.69 ml, 9.5 mmol) was added dropwise to methanol (20 ml at −10° C.). p-Nitro-L-phenylalanine (compound 1, 1.00 g, 4.76 mmol) was added, and the solution was stirred 24 hours. After evaporating to dryness the residue was recrystallized from methanol/ether giving 1.00 g (81%) of a white solid melting at 218°–219° C.; $[\alpha]_D^{25} = +11.5°$ (c=0.9, H₂O).

N$^\alpha$-Acetyl-p-Nitro-L-Phenylalanine Methyl Ester (3)

Compound 2 (4.10 g, 15.7 mmol) was suspended in a mixture of distilled pyridine (40 ml) and acetic anhydride (5 ml). A solution formed after several minutes, and stirring was continued overnight. The solvent was evaporated, and the residue was dissolved in ethyl acetate. The solution was then extracted with 0.1N HCl, 1M sodium bicarbonate, and water and dried (MgSO₄). Precipitation with hexanes gave 3.57 g (85.1%) of a solid melting at 113°–117° C. Recrystallization from ethyl acetate/hexanes gave 2.75 g, mp 118°–120° C., $[\alpha]_D^{25} = +15.1°$ (c=2.1, ethanol).

N$^\alpha$-Acetyl-p-Nitro-L-Phenylalanyl-3-Hydroxypropylamide (4)

Compound 3 (0.33 g, 1.2 mmol) and 3-amino-1-propanol (1.5 ml, 20 mmol) were dissolved in methanol (12 ml) and stirred for 12 hours under N$_2$ at room temperature. The solution was loaded onto a column (2×8 cm) of Dowex 50×8 in the hydrogen form and eluted with methanol. Evaporation of the solvent left a light yellow solid which was recrystallized from ethyl acetate/hexanes. Yield 0.29 g (75%) mp 206.5°–207° C. $[\alpha]_D^{26} = +14.8$ (c=1.4, ethanol). Anal. calc. for C$_{14}$H$_{19}$N$_3$O$_5$ (309.52): C, 54.36; H, 6.19; N, 13.58. Found: C, 54.44; H, 6.01; N, 13.55.

N$^\alpha$-Acetyl-p-(6-Oxo-n-Heptanoylamino)-L-Phenylalanyl-3-Hydroxypropylamide (5)

Compound 4 (701 mg, 2.27 mmol) was dissolved in methanol and hydrogenated overnight in a Parr shaker at 50 psi. with 10% palladium on charcoal as catalyst. Reduction was complete by TLC (chloroform/methanol/acetic acid: 70/25/5). The catalyst was removed by filtration, and the solvent was evaporated under vacuum leaving a clear, glassy solid. The amine was dissolved in dimethylformamide (30 ml). 6-Oxo-n-heptanoic acid (327 mg, 2.27 mmol) and dicyclohexylcarbodiimide (0.52 g, 1.1 equiv) were added, and the solution was stirred overnight at room temperature. After removal of dicyclohexylurea by filtration, the solvent was evaporated in vacuo at 40° C. The residue was chromatographed on a silica gel column (3×50 cm) eluting with a stepwise gradient of 5% to 10% methanol in chloroform. Yield 207 mg (23%) of a waxy, white solid melting at 142°–147° C. The melting point was raised to 157°–159° C. by recrystallization from methanol/ether. $[\alpha]_D^{23} = +8.2$ (c=1.0, methanol). Anal. calc. for C$_{21}$H$_{31}$N$_3$O$_5$(405.50): C, 62.20; H, 7.71; N, 10.36. Found: C, 61.92; H, 7.98; N, 10.09.

p-Nitro-D-Phenylalanine (6)

D-Phenylalanine (12.0 g, 73 mmol) and potassium nitrate (11 g, 109 mmol) were loaded into a teflon HF apparatus commonly used for the deprotection of peptides. The mixture was treated with liquid HF at approximately 0° C. for one hour. After removal of the HF by vacuum, the residue was dissolved in water and treated with concentrated ammonia until pH 6. The precipitate was recrystallized from hot water. Yield 9.31 g (61%) of a nearly white solid, mp 236.5°–237° C., $[\alpha]_D^{25} = -8.63°$ (c=1.7, 1N HCl).

N$^\alpha$-Acetyl-p-Nitro-D-Phenylalanine (7)

Compound 6 (6.20 g) was acetylated with acetic anhydride (9 ml) in aqueous sodium hydroxide at pH 9 and 4° C. according to the procedure of Yoshida and Ishii [J. Biochem., 71, 185–191 (1972)]. Obtained 5.32 g (71.4%), mp 165°–166° C., $[\alpha]_D^{25} = -46.2°$ (c =2.8, ethanol)

N$^\alpha$-Acetyl-p-Nitro-D-Phenylalanine Methyl Ester (8)

Compound 7 was dissolved in tetrahydrofuran (120 ml) and cooled in an ice bath. Diazomethane was generated by addition of N-nitrosomethylurea to an ice cold, equivolume mixture of ether and 40% aqueous potassium hydroxide. The diazomethane solution was added without purification to the stirred solution of the amino acid derivative. The reaction was complete when N$_2$ was no longer evolved upon addition of diazomethane. Excess diazomethane was consumed by the addition of acetic acid. The solution was extracted successively with saturated saline, 1M sodium bicarbonate, 0.1M HCl, and again with saline and dried (MgSO$_4$). Evaporation left 3.56 g (88.4%) of a solid melting at 110°–112° C. which was pure by TLC (chloroform/methanol acid: 85/10/5). $[\alpha]_D^{25} = -13.8$ (c=2.1, ethanol)

N$^\alpha$-Acetyl-p-Nitro-D-Phenylalanyl-3-Hydroxypropylamide (9)

The procedure for compound 4 was used to form the D-isomer, 9, from compound 8 (1.55 g). Yield 1.32 g (70%), mp 202.5°–204°, $[\alpha]_D^{26} = -13.8$ (c=1.1, ethanol). Anal. calc. for C$_{14}$H$_{19}$N$_3$O$_5$ (309.32): C, 54.36; H, 6.19; N, 13.58. Found: C, 53.93; H, 6.09; N, 13.48.

N$^\alpha$-Acetyl-p-Amino-D-Phenylalanyl-3-Hydroxypropylamide (10) and N-Acetyl-p-(6-Oxo-n-Heptanoylamino)-D-Phenylalanyl-3-Hydroxypropylamide (11)

Compound 9 (623 mg, 2.0 mmol) was hydrogenated and coupled to 6-oxo-n-heptanoic acid, by the procedure used to prepare the L-isomer 5. Column chromatography provided 11 (63.9 mg, 7.8%,) by TLC with chloroform/methanol/acetic acid (50/50/5), and unreacted compound 10 (255 mg, 45% recovered). Compound 11 had mp 137°–138.5° C. and $[\alpha]_D^{26} = -17.8°$ (c=1.0, ethanol).

N$^\alpha$-t-Butyloxycarbonyl-p-Nitro-L-Phenylalanine (12)

p-Nitro-L-phenylalanine (1) 51.3 g, 245 mmol) was stirred in ice cold sodium hydroxide (1N, 245 ml). Dioxane (400 ml) and di-t-butyldicarbonate (Fluka, 60.0 g, 275 mmol) were added. After stirring overnight in the cold, the dioxane was evaporated in vacuo. The mixture was cooled, acidified to pH 2 with sodium bisulfate (1N), and extracted with ethyl acetate (3×). The combined extracts were washed with water, dried (MgSO$_4$), and evaporated. Recrystallization from ethyl acetate/hexanes gave 60.7 g (80.2%) of compound 12 mp 105°–107° C., $[\alpha]_D^{26} = +25.4$ (c=1.1, 1M sodium bicarbonate).

N$^\alpha$-t-Butyloxycarbonyl-p-Nitro-L-Phenylalanyl-Glycine Benzyl Ester (13)

The carboxylic acid component (12, 10.0 g, 32.2 mmol) was dissolved in dry tetrahydrofuran (100 ml) in a 250 ml round-bottom flask equipped with a drying tube. N-methylmorpholine (3.54 ml. 1 equivalent) was added, and the solution was cooled to −15° C. in a bath of dry ice/isopropanol. Isobutyl chloroformate (4.18 ml, 1 equivalent) was added slowly to the stirred solution. The flask was allowed to warm to room temperature to insure complete formation of the mixed anhydride. A solution of glycine benzyl ester p-toluenesulfonate (Bachem, 10.9 g, 32.2 mmol) in dry tetrahydrofuran (100 ml) was cooled to −15° C., and treated with one equivalent of N-methylmorpholine. The flask containing the mixed anhydride was again cooled to −15°, and to it was added the glycine derivative. The mixture was allowed to reach room temperature and stirred for an hour or more. The solvent was then evaporated, and the residue was suspended in ethyl acetate. The mixture was then washed successively with HCl (0.1 N), saturated sodium bicarbonate, and water. After drying (MgSO$_4$) and filtering, the solution was evaporated to dryness. The solid residue was recrystallized from chloroform/hexanes. Yield 12.14 g (82.4%), mp 115°–118.5° C., $[\alpha]_D^{25} = -7.90°$ (c=1.8, chloroform). Anal. calc. for $C_{23}H_{27}N_3O_7$ (457.45): C, 60.39; H, 5.95; N, 9.19. Found: C, 60.42; H, 6.07; N, 9.11.

$N^\alpha$-Acetyl-p-Nitro-L-Phenylalanyl-Glycine Benzyl Ester (14)

The dipeptide (13, 1.73 g, 3.78 mmol) was dissolved in dry methylene chloride (5 ml) in a 25 ml round-bottom flask equipped with a drying tube The flask was cooled in an ice bath. Anhydrous trifluoroacetic acid (Aldrich, 5 ml) was added, and the solution was stirred at room temperature. After one hour the solvent was evaporated under reduced pressure leaving an oil. Successive addition of ether followed by either evaporation or decantation caused the residue to solidify. It was then placed under high vacuum to remove traces of trifluoroacetic acid.

The trifluoroacetate salt was dissolved in a mixture of dry tetrahydrofuran (10 ml) and distilled pyridine (2 ml). The solution was ascertained not to be strongly or moderately acidic and then treated with acetic anhydride (0.50 ml, 5.3 mmol). Product precipitated while the reaction continued overnight. Dry ether was added to complete the precipitation. The product was collected by vacuum filtration and washed thoroughly with ether. Yield 1.36 g (90%), recrystallized from acetone to give mp 180.5°–181° C., $[\alpha]_D^{26} = -3.9°$ (c=1.1, dioxane).

$N^\alpha$-Acetyl-p-Amino-L-Phenylalanyl-Glycine Benzyl Ester (15)

Compound 14 (267 mg, 0.67 mmol) was dissolved in methanol (50 ml). Platinum dioxide (3% of weight of peptide) was added, and the mixture was hydrogenated at atmospheric pressure. After 4 hours TLC (chloroform/methanol/acetic acid: 85/10/5) showed a clean conversion to the amine. The catalyst was separated by decantation, and the solvent was removed under reduced pressure. Compound 15 was obtained in nearly quantitative yield as a glassy solid.

$N^\alpha$-Acetyl-p (6-Oxo-n-Heptanoylamino)-L-Phenylalanyl-Glycyl-Methylamide (16)

Compound 15 (0.31 g, 0.63 mmol) was dissolved in a minimal amount of methanol (75 ml) by warming and the solution then cooled in an ice bath. Methylamine gas (Matheson) was passed through a sodium hydroxide drying tube into the solution. When saturation by the gas was approached (considerable gain in volume) the flask was stoppered and stored overnight at room temperature. Evaporation left a clear oil, which was redissolved in methanol. A precipitate was formed through the addition of chloroform and dry ether. The product was collected on a fine glass filter. Residual methylamine as detected by TLC (chloroform/methanol/acetic acid: 50/50/5) could not be removed in vacuo, but only by reprecipitation. Yield 180 mg (69%), mp 201°–203° C., $[\alpha]_D^{26} = +31.9°$ Anal. Calc. for $C_{21}H_{30}N_4O_5 \cdot H_2O$: C, 57.78: H, 7.39; N, 12.84. Found C, 57.55; H, 7.06; N, 12.91.

$N^\alpha$-Acetyl-p-(6-Oxo-n-Heptanoylamino)-L-Phenylalanyl-Glycine Benzyl Ester (17)

The mixed anhydride coupling was performed as described for the synthesis of compound 13 with 6-oxo-n-heptanoic acid (97 mg, 0.67 mmol) and the product from above, compound 15 (238 mg, 0.67 mmol). Each component was dissolved in 10 ml of dry tetrahydrofuran. Yield 111 mg (34%), mp 177.5°–180.5° C., $[\alpha]_D^{25} = +19.5$ (c.=1.4, methanol). Anal. calc. for $C_{27}H_{33}N_3O_6$ (493.58): C, 65.44; H, 6.71; N, 8.48. Found: C, 65.46; H, 6.74; N, 8.61.

$N^\alpha$-t-Butyloxycarbonyl-p-Nitro-L-Phenylalanyl-Glycyl-Methylamide (18)

Compound 13 (7.73 g, 16.9 mmol) in methanol (350 ml) was treated with methylamine as described for the synthesis of compound 16. The solvent was evaporated from the reaction mixture leaving a yellow solid, which was recrystallized from chloroform/hexanes. Yield 6.04 g (94.0%), mp 182°–184° C., $[\alpha]_D^{25} = +6.0°$ (c=1.0, methanol). Anal. calc. for $C_{17}H_{24}N_4O_6$ (380.40): C, 53.86; H, 6.36; N, 14.73. Found: C, 53.73; H, 6.45; N, 14.72.

$N^\alpha$-t-Butyloxycarbonyl-p-(6-Oxo-n-Heptanoylamino)-L-Phenylalanyl-Glycyl-Methylamide (19)

Compound 18 (5.28 g, 13.9 mmol) was dissolved in methanol (150 ml) and hydrogenated overnight at 1–3 Atm. using 10% palladium on charcoal catalyst (10% of weight of peptide). The catalyst was removed by filtration through Celite. The solvent was evaporated leaving a glassy solid, which was used without further purification.

6-Oxo-n-heptanoic acid (2.00 g, 13.9 mmol) was coupled by the mixed anhydride procedure as described for compound 13. Yield 5.87 g (89%) of a clear glass, which was homogeneous by TLC (chloroform/methanol/acetic acid: (85/10/5). $[\alpha]_D^{26} = +23.8°$ (c=1.2, methanol).

$N^\alpha$-t-Butyloxycarbonyl-$\gamma$-Benzyl-L-Glutamyl-p-(6-Oxo-n-Heptanoylamino)-L-Phenylalanyl-Glycyl-Methylamide (20)

Compound 19 (570 mg, 1.2 mmol) was deprotected as described for the synthesis of compound 14. The amine trifluoroacetate salt was dissolved in dry tetrahydrofuran (11 ml) and neutralized with N-methylmorpholine. Then $N^\alpha$-t-butyloxycarbonyl-$\gamma$-benzyl-L-glutamic acid (Bachem, 408 mg, 1.2 mmol) and dicyclohexylcarbodiimide (0.3 g, 1.5 mmol) were added. After stirring overnight the mixture was filtered and the solvent was evaporated. The residue was redissolved in chloroform and washed with 0.1N HCl, satd. sodium bicarbonate, and satd. sodium chloride. The organic phase was dried over magnesium sulfate, filtered, and evaporated. The residue was recrystallized from chloroform/hexanes. Yield 538 mg (66%), mp 114.5°–118° C., $[\alpha]_D^{26} = -17.8$ (c=1.1, metnanol). Anal. calc. for $C_{36}H_{49}N_5O_9 \cdot \frac{1}{2}H_2O$: C, 61.35; H, 7.15, N, 9.94. Found: C, 61.53; H, 6.95; N, 9.97.

$N^\alpha$-Acetyl-$\gamma$-Benzyl-L-Glutamyl-p-(6-Oxo-n-Heptanoylamino)-L-Phenylalanyl-Glycyl-Methylamide (21)

Compound 20 (444 mg, 0.638 mmol) was deprotected with trifluoroacetic acid in methylene chloride (10 ml, each) according to the procedure for compound 14. The amine trifluoroacetate salt was dissolved in a mixture of tetrahydrofuran (20 ml) and distilled pyridine (2.0 ml). Acetic anhydride (0.25 ml, 2.6 mmol) was added. After stirring for three hours the precipitate was collected on a fine glass filter and washed with tetrahydrofuran. Yield 361 mg (89%) of a white solid melting at 187°–190° C., which was pure by TLC (chloroform-/methanol/acetic acid: 70/25/5). $[\alpha]_D^{26}=6.1°$ (c=1.0, DMSO). $N^\alpha$-Acetyl-N'-Methyl-L-Glutaminyl-p-(6-Oxo-n-Heptanoylamino)-L-Phenylalanyl-Glycyl-Methylamide (22)

Compound 21 (122 mg, 0.19 mmol) was treated with methylamine in methanol (50 ml) according to the procedure for compound 16. Yield 86 mg (80%), mp 210°–214° C., $[\alpha]_D^{25}=-22.5°$ (c=1.3, H$_2$O). Anal. calc. for $C_{27}H_{40}N_6O_8 \cdot H_2O$: C, 56.04; H, 7.32; N, 14.52. Found: C, 56.21; H, 7.28; N, 14.30.

Similar techniques to those illustrated above can be utilized to prepare any desired monodisperse peptide carrier for use in preparing the conjugates of the invention.

Preparation of Conjugates

The following examples illustrate the general methods used for the preparation of conjugates. The carriers were monodisperse peptides and the drug was norepinephrine:

$N^\alpha$-t-Butyloxycarbonyl-p-[6-($\beta$-3',4'-Dihydroxyphenyl-$\beta$-Hydroxy)-Ethylamino-n-Heptanoylamino]-L-Phenylalanyl-Glycyl-Methylamide (23)

Method A

The peptide derivative 19 (239 mg, 0.50 mmol) and DL-norepinephrine (85 mg, 0.50 mmol) were dissolved in acetic acid (2 ml) and hydrogenated for two days at atmospheric pressure and room temperature over platinum dioxide catalyst (2–20% of weight of peptide). The solution was decanted from the catalyst and added to cold dilute hydrochloric acid (0.01N, 50 ml). Extractions with chloroform and then with n-butanol were performed. The combined butanol extracts were washed with saline until neutral and evaporated under vacuum at less than 40° C. The residue was extracted with n-butanol (3×), filtered, and evaporated. The resulting oil was solidified by trituration with ether giving 230 mg of the hydrochloride salt of the title compound. This was then purified by HPLC. Yield 49% of the dihydrogen phosphate salt.

Method B

Compound 19 (2.56 g, 5.4 mmol) and DL-norepinephrine hydrochloride (1.19 g, 5.8 mmol) were dissolved in methanol (100 ml) containing acetic acid (0.5 ml). Sodium cyanoborohydride (0.46 g, 7.3 mmol) in methanol (20 ml) was added dropwise, and the solution was heated at 40° C. for 20 hours. Hydrochloric acid (0.1N, 200 ml) was added at 10° C., and the solution was degassed under suction from a water aspirator. The solution was extracted with chloroform (3×). Concentrated sodium chloride was added and the product was extracted with n-butanol as described in Method A. The residue was purified by flash chromatography (55×150 mm column, eluting with a gradient of 4 to 15 parts methanol in 50 parts chloroform and 5 parts acetic acid). The eluate was reduced to one-tenth the original volume in vacuo and added to cold 0.1N HCl. The product was extracted and solidified as described in Method A giving 1.46 g (41%) of the hydrochloride salt of the title compound. $[\alpha]_D^{26}=+6.2°$ (c=1.5, H$_2$O). Anal. calc. for $C_{32}H_{48}N_5O_8Cl.2/3BuOH.4/3H_2O$: C, 56.29; H, 7.81; N, 9.47. Found: C, 56.28; H, 7.86; N, 9.41.

$N^\alpha$-Acetyl-p-[6-($\beta$-3',4-Dihydroxyphenyl-$\beta$-Hydroxy)-Ethylamino-n-Heptanoylamino]-L-Phenylalanyl-Glycyl-Methylamide (24)

Method C

The peptide derivative 16 (24 mg, 57 mol) and DL-norepinephrine (9.7 mg, 57 μmol) were hydrogenated as described in Method A. The reaction mixture was chromatographed on preparative TLC (silica, chloroform/methanol/acetic acid: 50/50/5). The product was identified on the plate by slight darkening due to oxidation, and by ultraviolet detection. The band was extracted with methanol, and the product was purified by HPLC. Yield 6.4 mg (17%) of the dihydrogen phosphate salt of the title compound.

$N^\alpha$-Acetyl-N'-Methyl-L-Glutaminyl-p-[6-($\beta$-3',4'-Dihydroxyphenyl-$\beta$-Hydroxy)-Ethylamino-n-Heptanoylamino]-L-Phenylalanyl-N'-Methyl-L-Glutaminyl-Methylamide (25)

Method D

The tripeptide derivative, $N^\alpha$-acetyl-N'-methyl-L-glutaminyl-p-(6-oxo-n-heptanoylamino)-L-phenylalanyl-N'-methyl-L-glutaminyl-methylamide (55 mg, 85 μmol) and DL-norepinephrine hydrochloride (35 mg, 170 μmol) were dissolved in pH 5 sodium acetate buffer (0.2M, 6 ml). Sodium cyanoborohydride (38 mg, 0.60 mmol) in methanol (6 ml) was added, and the mixture was heated at 60° C. for 48 hours. Most of the solvent was then removed by evaporation, and hydrochloric acid (0.2N, 5 ml) was added. The mixture was filtered and applied to a Bio-gel P-2 column (1.6×75 cm) in the cold. The material was eluted with 0.01N HCl. The salt of the title compound (4 mg, 6%) eluted at 0.161$V_t$. The proton NMR spectrum of the product was identical to that of the same compound synthesized by Method C.

$N^\alpha$-t-Butyloxycarbonyl-tri-$\delta$-Hydroxy-L-$\alpha$-Aminovaleryl-p-[6-$\beta$-3',4'-Dihydroxyphenyl-$\beta$-Hydroxy)-Ethylamino-n-Heptanoylamino]-L-Phenylalanyl-Glycyl Methylamide (26)

Method E

DL-norephinephrine.HCl (9.5 mg, 46 mol) containing $^{14}$C-labeled tracer and a pentapeptide derivative $N^\alpha$-t-butyloxycarbonyl-tri-($\delta$-hydroxy-L-$\alpha$-aminovaleryl)-p-(6-oxo-n-heptanoylamino)-L-phenylalanyl-glycyl-methylamide (19.2 mg, 23 μmol) were dissolved in a mixture of methanol (4.5 ml) and 0.2N sodium acetate (pH 5) buffer. The solution was evaporated to a small volume, and n-butanol (3 ml) was added. Half of the volume of solvent then was removed in vacuo at 40° C. A solution of sodium cyanoborohydride (14 mg, 0.22 mol) in methanol (1 ml) was added, and the solution was warmed at 50° C. for 48 hours. The precipitate was removed by centrifugation and the product was isolated by reversed phase HPLC. Yield 10 mg (40%) of the dihydrogen phosphate salt of the title compound. The specific activity of the product was within 3% of that measured for the starting material.

Biological Activity—in vitro

The biological activity of the conjugates of the invention was tested in a wild type S49 cell assay. The assay is indicative of the relative beta adrenergic activity of the compound. The activity of each conjugate tested was compared to the activity of isoproterenol as the base standard.

In the test, S49 cells were centrifuged and then resuspended (2 to $2.5 \times 10^6$ cells per ml.) in Dulbecco's modified Eagle medium (13.3 g per liter) and 20 mM Hepes (pH 7.4)+0.1% bovine serum albumin. The S49 suspensions were incubated at 37° C. for 10 minutes without the conjugate and then added to tubes with or without the conjugate for an additional 6 minutes. The reaction was stopped by cooling on ice. Incubation without the conjugates present established a base line.

After isolation of a pellet of cells by centrifugation they were resuspended and boiled. Aliquots were then used for the competitive binding assay for cyclic AMP described by Gilman in the Procedings of the National Academy of Sciences USA 67, 305-312 (1970). Results were plotted as pmol cyclic AMP accumulated per $10^7$ cells in excess of base line as a function of the log of the concentration of the analog.

The results in vitro testing of some typical conjugate compounds is set forth in Table 2 below:

TABLE 2

In Vitro Biological Activity[a] of Peptide Conjugates of Isoproterenol.

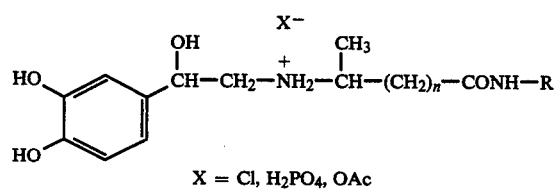

$X = Cl, H_2PO_4, OAc$

| compound | R[b] | Activity relative to isoproterenol |
|---|---|---|
| A | Ac—L-Phe—HPA | 4 $9.0 \times 10^{-2}$ |
| B | Ac—D-Phe—HPA | 4 $4.0 \times 10^{-1}$ |
| C | Ac—Phe—Gly—OH | 4 $4.4 \times 10^{-1}$ |
| D | Ac—Phe—Gly—NHCH$_3$ | 4 1.1 |
| E | Boc—Phe—Gly—NHCH$_3$ | 4 4.1 |
| F | H—Phe—Gly—NHCH$_3$ | 4 $1.3 \times 10^{-4}$ |
| G | Boc—Gly—Phe—NHCH$_3$ | 4 $6.8 \times 10^{-1}$ |
| H | Ac—Glu(NHCH$_3$)—Phe—Gly—NHCH$_3$ | 4 $3.7 \times 10^{-6}$ |
| I | Ac—Hyv—Phe—Gly—NHCH$_3$ | 4 $8.0 \times 10^{-5}$ |
| J | Ac—Cit—Phe—Gly—NHCH$_3$ | 4 $5.5 \times 10^{31\,2}$ |
| K | Boc—Cit—Phe—Gly—NHCH$_3$ | 4 $3.8 \times 10^{-5}$ |
| L | Ac—Glu(NHCH$_3$)—Phe—Glu(NHCH$_3$)$_2$ | 3 $4.5 \times 10^{-6}$ |
| M | Ac—Glu(NHCH$_3$)—Phe—Glu(NHCH$_3$)$_2$ | 4 $2.3 \times 10^{-5}$ |
| N | Ac—Glu(NHCH$_3$)—Phe—Glu(NHCH$_3$)$_2$ | 5 $8.6 \times 10^{-6}$ |
| O | Boc—Hyv$_3$—Phe—Gly—NHCH$_3$ | 4 1.0 |
| P | Boc—Phe—Hyv$_3$—Gly—NHCH$_3$ | 4 $7.9 \times 10^{-1}$ |

[a]Biological activity was measured by cyclic AMP accumulation in S49 cells. Relative activity is expressed as the ration of K$_A$ for isoproterenol to K$_A$ for the compound.
[b]Abbreviations used: Ac = acetyl; Phe = phenylalanine; HPA = hydroxypropylamide; Gly = glycine; Boc = t-butyloxycarbonyl; Glu = glutamic acid; Hyv = δ-hydroxy-α-aminovaleric acid; Cit = citrulline

Biological Activity—in vivo

In addition to the in vitro testing set forth above, in vivo testing was also conducted on a number of conjugates of the invention. The tests were conducted by injecting various doses of the test conjugate into the femoral vein of rats and thereafter recording changes in heart rate, arterial pulse pressure and mean pressure.

More specifically, male Sprague-Dawley rats weighing 280-350 g had their femoral arteries connected to a Statham P-23 pressure transducer, which was in turn recorded on a Beckman Dynograph model R511A. Venus cannula were inserted in the femoral veins. Two syringes were attached to the veins via a 3-way stopcock. One syringe contained heparinized saline (40 units/ml) while the other contained the conjugate to be tested.

All cannulas were periodically flushed with the heparinized saline to prevent clots from forming. After the blood pressure and heart rate had stabilized, a volume of heparinized saline corresponding to the volume of drug conjugate the animal was to receive, was injected, and the response observed. Then various doses of the test drug conjugate were injected with a minimum interval of ten minutes between doses. The dose range was from 0.001 to 10.0 mg/kg, with the doses always being administered in increasing amounts. From the drug injections, a dose-response curve was obtained. The response curves were then compared to the animals' response to isoproterenol administered under the same conditions. Table 3 below presents the results of these in vivo tests:

TABLE 3

In Vivo Activity of Peptide Conjugates of Isoproterenol

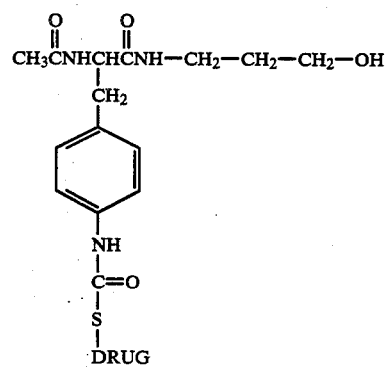

| Compound | R | In Vivo Activity[a] Relative to Isoproterenol |
|---|---|---|
| E | Boc—Phe—Gly—NHCH$_3$ | 3.74 |
| G | Boc—Gly—Phe—NHCH$_3$ | .92 |
| H | Ac—Glu(NHCH$_3$)—Phe—Gly—NHCH$_3$ | 1.77 |
| I | Ac—Hyv—Phe—Gly—NHCH$_3$ | 1.48 |
| J | Ac—Cit—Phe—Gly—NHCH$_3$ | .79 |
| K | Boc—Cit—Phe—Gly—NHCH$_3$ | .22 |
| O | Boc—Hyv$_3$—Phe—Cly—NHCH$_3$ | .76 |
| P | Boc—Phe—Hyv$_3$—Gly—NHCH$_3$ | .59 |

[a]Biological activity in vivo was measured as the effective dose that reduces rat blood pressure by 50%. Relative activity is expressed as the ratio of the molar ED$_{50}$ of isoproterenol to the molar ED$_{50}$ of the compound.

We claim:
1. A drug conjugate having the formula:

$$\begin{array}{c}
\text{O} \quad\quad\quad \text{O} \\
\| \quad\quad\quad\quad \| \\
CH_3CNHCHCNH-CH_2-CH_2-CH_2-OH \\
| \\
CH_2 \\
| \\
\text{[phenyl ring]} \\
| \\
NH \\
| \\
C=O \\
| \\
S \\
| \\
DRUG
\end{array}$$

wherein
S is a spacer grouping comprising a branched alkyl chain having from 2 to 6 carbon atoms in the non-branched portion of the alkyl chain and wherein the branched portion is a lower alkyl group having from 1–4 carbon atoms and wherein one end of the spacer grouping is covalently bound to the drug and the other end is covalently bound to

and wherein the branch of the spacer grouping is adjacent the drug; and

DRUG is selected from the group of sympathomimetic and autacoid drug moieties.

2. The conjugate of claim 1 wherein:

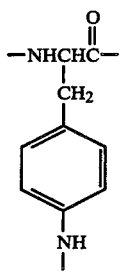

is in the levo-configuration.

3. The conjugate of claim 1 wherein:

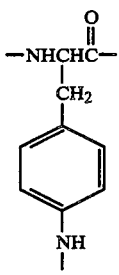

is in the dextro-configuration.

4. A drug conjugate having the formula:

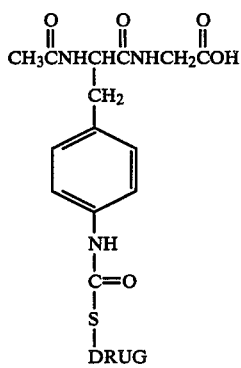

wherein
S is a spacer grouping comprising a branched alkyl chain having from 2 to 6 carbon atoms in the nonbranched portion of the alkyl chain and wherein the branched portion is a lower alkyl group having from 1-4 carbon atoms and wherein one end of the spacer grouping is covalently bound to the drug and the other end is covalently bound to

and wherein the branch of the spacer grouping is adjacent the drug; and

DRUG is selected from the group of sympathomimetic and autacoid drug moieties.

5. A drug conjugate having the formula:

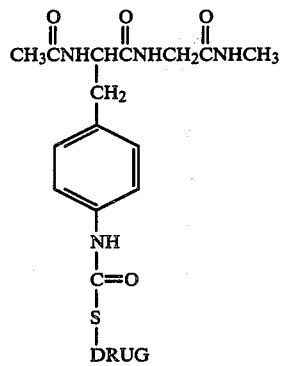

wherein
S is a spacer grouping comprising a branched alkyl chain having from 2 to 6 carbon atoms in the nonbranched portion of the alkyl chain and wherein the branched portion is a lower alkyl group having from 1-4 carbon atoms and wherein one end of the spacer grouping is covalently bound to the drug and the other end is covalently bound to

and wherein the branch of the spacer grouping is adjacent the drug; and

DRUG is selected from the group of sympathomimetic and autacoid drug moieties.

6. A drug conjugate having the formula:

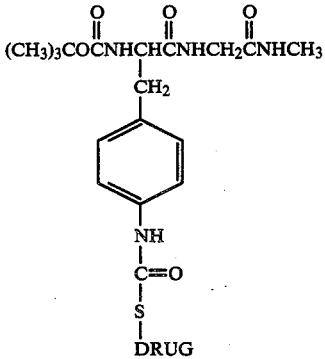

wherein
S is a spacer grouping comprising a branched alkyl chain having from 2 to 6 carbon atoms in the nonbranched portion of the alkyl chain and wherein the branched portion is a lower alkyl group having from 1-4 carbon atoms and wherein one end of the spacer grouping is covalently bound to the drug and the other end is covalently bound to

and wherein the branch of the spacer grouping is adjacent the drug; and

DRUG is selected from the group of sympathomimetic and autacoid drug moieties.

7. A drug conjugate having the formula:

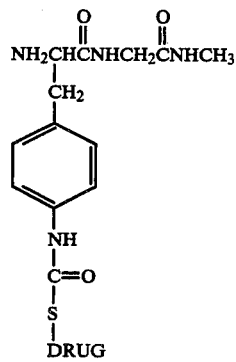

wherein

S is a spacer grouping comprising a branched alkyl chain having from 2 to 6 carbon atoms in the non-branched portion of the alkyl chain and wherein the branched portion is a lower alkyl group having from 1–4 carbon atoms and wherein one end of the spacer grouping is covalently bound to the drug and the other end is covalently bound to

and wherein the branch of the spacer grouping is adjacent the drug; and

DRUG is selected from the group of sympathomimetic and autacoid drug moieties.

8. A drug conjugate having the formula:

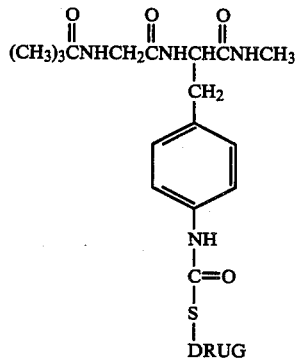

wherein

S is a spacer grouping comprising a branched alkyl chain having from 2 to 6 carbon atoms in the non-branched portion of the alkyl chain and wherein the branched portion is a lower alkyl group having from 1–4 carbon atoms and wherein one end of the spacer grouping is covalently bound to the drug and the other end is covalently bound to

and wherein the branch of the spacer grouping is adjacent the drug; and

DRUG is selected from the group of sympathomimetic and autacoid drug moieties.

9. A drug conjugate having the formula:

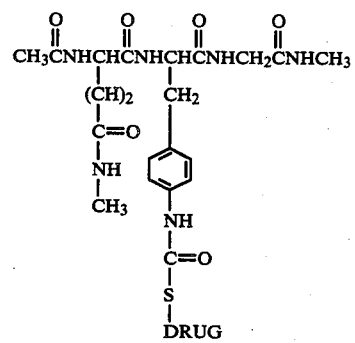

wherein

S is a spacer grouping comprising a branched alkyl chain having from 2 to 6 carbon atoms in the non-branched portion of the alkyl chain and wherein the branched portion is a lower alkyl group having from 1–4 carbon atoms and wherein one end of the spacer grouping is covalently bound to the drug and the other end is covalently bound to

and wherein the branch of the spacer grouping is adjacent the drug; and

DRUG is selected from the group of sympathomimetic and autacoid drug moieties.

10. A drug conjugate having the formula:

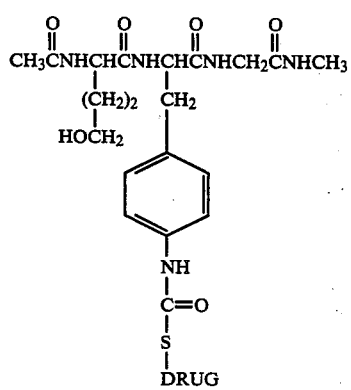

wherein

S is a spacer grouping consisting a branched alkyl chain having from 2 to 6 carbon atoms in the non-branched portion of the alkyl chain and wherein the branched portion is a lower alkyl group having from 1–4 carbon atoms and wherein one end of the spacer grouping is covalently bound to the drug and the other end is covalently bound to

and wherein the branch of the spacer grouping is adjacent the drug; and

DRUG is selected from the group of sympathomimetic and autacoid drug moieties.

11. A drug conjugate having the formula:

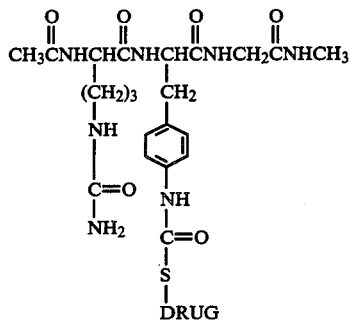

wherein

S is a spacer grouping comprising a branched alkyl chain having from 2 to 6 carbon atoms in the non-branched portion of the alkyl chain and wherein the branched portion is a lower alkyl group having from 1–4 carbon atoms and wherein one end of the spacer grouping is covalently bound to the drug and the other end is covalently bound to

and wherein the branch of the spacer grouping is adjacent the drug; and

DRUG is selected from the group of sympathomimetic and autacoid drug moieties.

12. A drug conjugate having the formula:

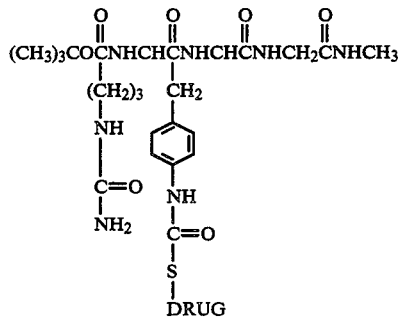

wherein

S is a spacer grouping comprising a branched alkyl chain having from 2 to 6 carbon atoms in the non-branched portion of the alkyl chain and wherein the branched portion is a lower alkyl group having from 1–4 carbon atoms and wherein one end of the spacer grouping is covalently bound to the drug and the other end is covalently bound to

and wherein the branch of the spacer grouping is adjacent the drug; and

DRUG is selected from the group of sympathomimetic and autacoid drug moieties.

13. A drug conjugate having the formula:

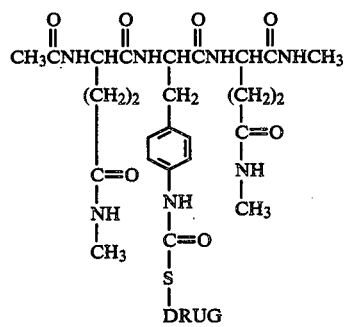

wherein

S is a spacer grouping comprising a branched alkyl chain having from 2 to 6 carbon atoms in the non-branched portion of the alkyl chain and wherein the branched portion is a lower alkyl group having from 1–4 carbon atoms and wherein one end of the spacer grouping is covalently bound to the drug and the other end is covalently bound to

and wherein the branch of the spacer grouping is adjacent the drug; and

DRUG is selected from the group of sympathomimetic and autacoid drug moieties.

14. A drug conjugate having the formula:

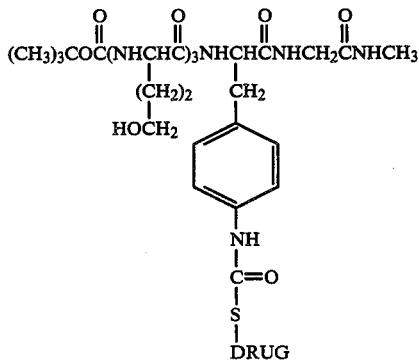

wherein

S is a spacer grouping comprising a branched alkyl chain having from 2 to 6 carbon atoms in the non-branched portion of the alkyl chain and wherein the branched portion is a lower alkyl group having from 1–4 carbon atoms and wherein one end of the spacer grouping is covalently bound to the drug and the other end is covalently bound to

and wherein the branch of the spacer grouping is adjacent the drug; and

DRUG is selected from the group of sympathomimetic and autacoid drug moieties.

15. A drug conjugate having the formula:

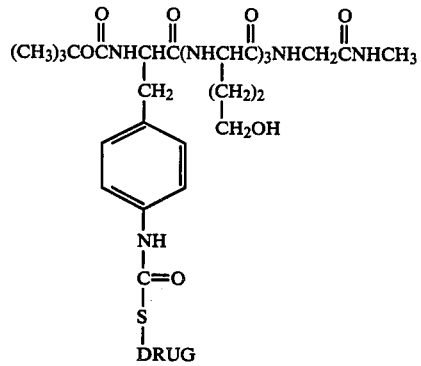

wherein
S is a spacer grouping comprising a branched alkyl chain having from 2 to 6 carbon atoms in the non-branched portion of the alkyl chain and wherein the branched portion is a lower alkyl group having from 1–4 carbon atoms and wherein one end of the spacer grouping is covalently bound to the drug and the other end is covalently bound to

and wherein the branch of the spacer grouping is adjacent the drug; and
DRUG is selected from the group of sympathomimetic and autacoid drug moieties.

16. As a composition of matter, the compound $N^{\alpha}$-t-butyloxy carbonyl-p-[6-($\beta$-3',4'-dihydroxyphenyl-$\beta$-hydroxy)-ethylamino-n-heptanoylamino]-L-phenylalanyl-glycyl-methylamide.

* * * * *

UNITED STATES PATENT AND TRADEMARK OFFICE
CERTIFICATE OF CORRECTION

PATENT NO. : 4,587,046
DATED : May 6, 1986
INVENTOR(S) : Murray Goodman et al.

It is certified that error appears in the above-identified patent and that said Letters Patent is hereby corrected as shown below:

Column 17, line 62, the formula: "$C_{21}H_{304}O_5 \cdot H_2O$"

should read: "$C_{21}H_{30}N_4O_5 \cdot H_2O$"

UNITED STATES PATENT AND TRADEMARK OFFICE
CERTIFICATE OF CORRECTION

PATENT NO. : 4,587,046

DATED : May 6, 1986

INVENTOR(S) : Murray Goodman et al.

It is certified that error appears in the above-identified patent and that said Letters Patent is hereby corrected as shown below:

Column 25, lines 47-61, the structure in Claim 8 should be:

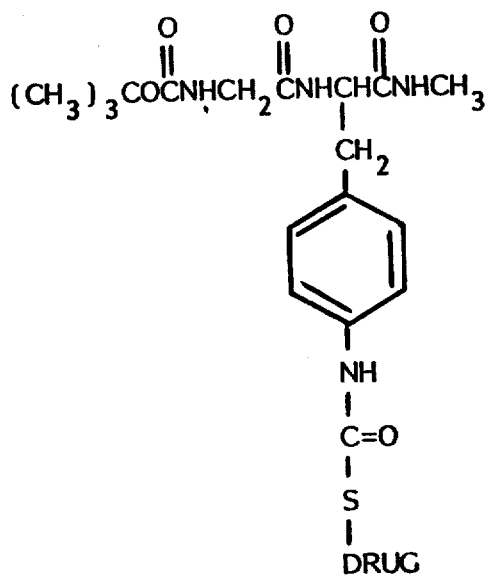

Signed and Sealed this

Fourteenth Day of October, 1986

[SEAL]

Attest:

DONALD J. QUIGG

Attesting Officer

Commissioner of Patents and Trademarks